United States Patent [19]

Liu

[11] Patent Number: 4,781,865

[45] Date of Patent: Nov. 1, 1988

[54] PHOSPHINATED AND PHOSPHONATED SULFONIC ACIDS

[75] Inventor: Chung-Tsing Liu, Bloomington, Minn.

[73] Assignee: Ecolab, Inc., St. Paul, Minn.

[21] Appl. No.: 913,023

[22] Filed: Sep. 29, 1986

[51] Int. Cl.⁴ ............................................. C07F 9/02
[52] U.S. Cl. .............................. 260/502.5 D; 558/45; 260/502.5 G; 260/501.15; 260/501.21
[58] Field of Search ............... 260/503, 507 R, 513 N, 260/501.5, 501.21, 502.5 D, 502.5 G; 558/45

[56] References Cited

U.S. PATENT DOCUMENTS

| | | | |
|---|---|---|---|
| 2,983,712 | 5/1961 | Wilkinson | 260/79.3 |
| 3,506,707 | 4/1970 | Miller et al. | 260/513 |
| 3,544,597 | 12/1970 | Killam | 260/332.1 |
| 3,654,348 | 4/1972 | Robson et al. | 260/508 |
| 3,926,821 | 12/1975 | LeSuer | 252/46.7 |
| 4,000,188 | 12/1976 | Dear et al. | 260/513 N |
| 4,014,926 | 3/1977 | Dear et al. | 260/513 N |
| 4,026,812 | 5/1977 | LeSuer | 252/75 |
| 4,090,967 | 5/1978 | Falk | 252/3 |
| 4,212,734 | 7/1980 | Redmore et al. | 210/58 |
| 4,216,163 | 8/1980 | Sommer et al. | 260/502.5 |
| 4,432,879 | 2/1984 | Greaves et al. | 210/699 |
| 4,590,014 | 5/1986 | Wolf et al. | 260/502.4 |

*Primary Examiner*—Nicky Chan
*Attorney, Agent, or Firm*—Merchant, Gould, Smith, Edell, Welter & Schmidt

[57] ABSTRACT

Phosphinated or phosphonated sulfonic acid compounds are prepared by a process comprising reacting a hypophosphite salt, such as an alkali metal hypophosphite, with an alkenyl sulfonic acid compound of the formula $CH_2=C(R)C(O)NH-Z-SO_3-M^+$, wherein Z is a divalent ($C_1-C_{18}$)hydrocarbyl group, R is H or ($C_1-C_7$)alkyl and $M^+$ is $H^+$, $NR_4^+$ or an equivalent metal cation, such as an alkali metal cation.

15 Claims, No Drawings

PHOSPHINATED AND PHOSPHONATED SULFONIC ACIDS

FIELD OF THE INVENTION

The invention relates to new compositions of matter which are useful to sequester water hardness factors. More particularly, the compositions of this invention are made by the reaction of hypophosphite salts with certain sulfo-containing compounds.

BACKGROUND OF THE INVENTION

Alkyl phosphinates can be prepared by the reaction of an olefin with an alkali metal salt of hypophosphorous acid. For example, the reaction of alpha-olefins with sodium hypophosphite yields sodium alkyl phosphinates when initiated photochemically or by an introduced chemical source of free radicals such as a peroxide. The reaction may be summarized as follows:

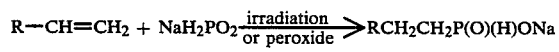

The alkyl phosphinate can be converted into the corresponding phosphonate ($RCH_2CH_2P(O)(ONa)_2$) by exposure to an oxidizing agent. Both the alkyl phosphonates and alkyl phosphinates can function as anionic surfactants, and can act to enhance the wetting power of aqueous media.

Commonly-assigned U.S. Pat. No. 4,590,014, discloses that high-yield reactions of an olefinic material with a hypophosphite salt to yield a phosphinate salt can be accomplished by a process comprising simultaneously adding the olefinic material and essentially all of the free radical source used to initiate the reaction to a hot solution of the hypophosphite salt. In preferred embodiments of the invention, an alcohol solution of the olefinic compound and the free radical source are added to the hypo-phosphite in an aqueous alcoholic reaction medium. During the addition, the hypophosphite solution is maintained at a temperature at or slightly above the decomposition temperature of the free radical source. After the addition is completed, the reaction mixture can be heated for a period of time sufficient to complete the reaction.

Commonly-assigned U.S. patent application Ser. No. 838,097, discloses that the photo-initiated reaction of an olefinic material with a hypophosphite salt to afford a phosphinate salt can be accomplished in high yields by a process comprising simultaneously adding the olefinic material and essentially all of the photo-initiator to a solution of the hypophosphite salt in an aqueous alcoholic reaction medium. During the addition, the hypophosphite solution is irradiated with a source of ultraviolet light. After the addition is completed, the reaction mixture is irradiated and heated for a period of time sufficient to complete the reaction.

Wolf (U.S. Pat. No. 4,590,014) and Ser. No. 838,097 also disclose that alkyl phosphinates prepared according to these processes strongly complex alkaline earth metal ions, i.e., calcium ion, and are more effective sequestering agents than the corresponding alkyl phosphonates. This result indicates that water-soluble alkyl phosphinates will be effective as builders and conditioners in detergent formulations, where they will function as substitutes or replacements for commonly-used sequestering agents such as citrates, hydroxy malonates, nitrilotriacetates and the like. These sequestering agents act to prevent or inhibit metal cations responsible for water hardness such as $Ca^{++}$ or $Mg^{++}$ from precipitating commonly-used alkali metal builder salts and anionic surfactants.

Therefore, a need exists for new phosphinated and phosphonated compounds which are effective to sequester water hardness factors.

SUMMARY OF THE INVENTION

The present invention is directed to compositions of matter comprising novel phosphinated and phosphonated sulfonic acids and the salts thereof. Preferred compounds of the present invention are highly soluble in both acidic and basic aqueous media, are substantially caustic-stable, and have high chelation values with respect to hardness ions. The compounds of the present invention are prepared by the free radical-initiated reaction of a hypophosphite salt with an alkenylamido sulfonic acid compound of the general formula I:

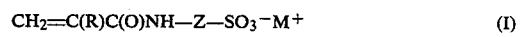

wherein R is H or ($C_1$-$C_7$)alkyl, Z is a divalent ($C_1$-$C_{18}$)hydrocarbyl group and $M^+$ is $H^+$, $NR_4^+$ or one equivalent of a metal cation. Preferably, the reaction is carried out under alkaline conditions and is initiated by the thermal decomposition of an organic free-radical source. The reaction of the hypophosphite salt with alkenylamido sulfonic acid compound (I) yields a monomeric phosphinated sulfonic acid compound of the general formula II:

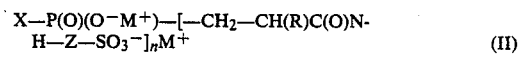

wherein x=H, n=1, and $M^+$, R and Z are as defined hereinabove. This compound can be oxidized to the corresponding phosphonated sulfonic acid compound of the general formula (III):

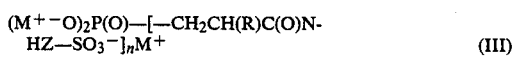

wherein $M^+$, R, Z and n are as defined hereinabove.

In compounds II and III, $M^+$ is preferably $H^+$, $NH_4^+$, an alkali metal cation or an alkaline earth metal cation; most preferably $H^+$ or $Na^+$. Z is preferably ($C_1$-$C_{18}$)alkylene, ($C_5$-$C_{10}$)cycloalkylene or ($C_6$-$C_{18}$)arylene. Other preferred Z and R moieties correspond to those set forth for compound I hereinbelow.

Although compounds of formulas II and III are effective sequestering agents, the reaction of a hypophosphite salt with a compound of formula I also yields substantial amounts of oligomeric and polymeric phosphino compounds of formula II, wherein: (a) X is H and n is greater than 1, e.g., is about 2–10 or more; and (b) wherein X is [—$CH_2$—CH(R)C(O)NH—$ZSO_3$—$]_nM^+$, wherein n is 1 or more, e.g., n is about 1–10 or more. Compounds wherein X=H and n is greater than one can also be oxidized to the corresponding phosphono compounds.

The complex reaction product of a hypophosphite salt with the sulfonic acid compound of formula I is itself useful as a sequestering agent in aqueous systems without further purification or resolution of the product into its individual components. For example, the complex reaction mixture obtained by reacting a hypophosphite salt with a sulfonic acid compound of formula I was found to be at least equivalent to a simple n-alkyl phosphonate in its ability to sequester calcium ion. Therefore, the present invention is also directed to this phosphinated reaction product and the corresponding phosphonated product as well as to substantially pure compounds of formulas II and III.

DETAILED DESCRIPTION OF THE INVENTION

Alkenylamido Sulfonic Acid Compound

Alkenylamido sulfonic acid compounds useful in the present invention are those of general formula I:

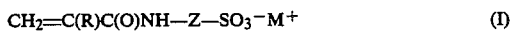
$$CH_2=C(R)C(O)NH-Z-SO_3^-M^+ \qquad (I)$$

wherein R is $(C_1-C_7)$alkyl, preferably $(C_1-C_4)$alkyl; Z is a divalent $(C_1-C_{18})$hydrocarbyl radical and $M^+$ is $H^+$, $NR_4^+$ or one equivalent of a metal cation.

Preferably, Z is $(C_1-C_{18})$alkylene, $(C_5-C_{10})$cycloalkylene or $(C_6-C_{18})$arylene. Preferred examples of alkylene moieties include: (a) n-alkylene moieties, e.g., methylene ($-CH_2-$), ethylene ($-CH_2-CH_2-$), propylene, butylene, and the like; (b) alkyl-substituted-n-alkylene moieties, most preferably those of the general formula $(R_1)(R_2)C-C(R_3)(R_4)$, wherein $R_1$, $R_2$, $R_3$ and $R_4$ are individually $(C_1-C_4)$alkyl or $C_5-C_{10}$-cycloalkyl; and (c) phenyl-substituted alkylene moieties of types (a) or (b), wherein the aryl group is phenyl, optionally substituted by about 1-3 $(C_1-C_4)$alkyl groups.

Preferred examples of $(C_5-C_{10})$cycloalkylene moieties include divalent cycloalkyl moieties such as cyclopentylene, cyclohexylene, cycloheptylene, cyclooctylene and the like. The cycloalkylene ring can optionally be attached to 1-2 $(C_1-C_4)$alkylene moieties to yield a divalent -cycloalkylene(alkylene)- or a -(alkylene)cycloalkylene(alkylene)- moiety.

Preferred arylene moieties include divalent aromatic moieties such as phenylene, naphthylene (naphthalendi-yl) and the like. The aromatic ring system can optionally be attached to 1-2 $(C_1-C_4)$alkylene moieties, e.g., isopropylene, methylene, ethylene, propylene and the like; to yield a divalent -arylene(alkylene)- or -(alkylene)arylene(alkylene)- moiety.

$M^+$ can be H, $NR_4^+$ or an equivalent metal cation. Such metal cations are derived from Groups I(A), I(B), II(A), II(B), III(A), and VIII of the periodic table. Preferably $M^+$ is $H^+$, $NH_4^+$ or an alkali metal cation such as sodium, lithium or potassium.

Preferably, the sulfonic acid compound of formula I can be represented by the formula:

$$CH_2=C(R)C(O)NHC(R_1)(R_2)C(R_3)(R_4)SO_3^-M^+$$

wherein R, $R_1$, $R_2$, $R_3$, $R_4$ and $M^+$ are as hereinabove described. Preferably R, $R_1$, $R_2$, $R_3$ and $R_4$ are H or $(C_1-C_4)$alkyl, most preferably H or methyl.

Alkenylamido sulfonic acids and their salts are well known in the art and have been thoroughly described; for example, in U.S. Pat. Nos. 2,983,712; 3,332,904; 3,506,707; 3,544,597; 4,026,812; British Pat. No. 1,090,779; Canadian Pat. No. 704,778; and German Offenlegungsschift No. 2,105,030, the disclosures of which are incorporated by reference herein. For example, U.S. Pat. No. 3,506,707 discloses the preparation of alkenylamido sulfonic acids by reacting an olefinic compound containing at least one allylic H with an acylhydrogen sulfate to form an intermediate which is reacted with water and $CH_2=C(R)CN$ in the presence of $H_2SO_4$.

Illustrative examples of compounds of formula I are listed on Table I, below.

TABLE I

2-Acrylamidoethanesulfonic acid
2-Acrylamidopropanesulfonic acid
1-Methacrylamidopropane sulfonic acid
2-Acrylamido-2-methylpropanesulfonic acid
2-Methacrylamido-2-methylpropanesulfonic acid
2-Acrylamidobutanesulfonic acid
3-Acrylamidobutane-2-sulfonic acid
3-Acrylamido-2,3-dimethylbutane-2-sulfonic acid
2-Acrylamido-2,4,4-trimethylpentanesulfonic acid
2-Acrylamido-2-phenylethanesulfonic acid
2-Acrylamido-2-phenylpropanesulfonic acid
2-Acrylamido-2-tolylethane sulfonic acid
2-Methacrylamidocyclohexane sulfonic acid
p-Methacrylamidobenzene sulfonic acid
6-Acrylamidonaphthalene-1-sulfonic acid Especially preferred is 2-acrylamido-2-methylpropanesulfonic acid, available commercially from the Lubrizol Corporation, Wickliffe, Ohio, as AMPS ™ monomer. The sulfonate salts of this and other alkenylamido sulfonic acids are readily formed by the reaction of the acid with either metallic or nitrogen bases in a suitable solvent such as water or dimethylformamide. For example, an aqueous solution of the sulfonic acid can be adjusted to about pH 9-12 with an aqueous solution of an alkali metal hydroxide such as sodium hydroxide. See AMPS ™ Monomer, Lubrizol Technical Bulletin (1981), the disclosure of which is incorporated by reference herein. This reaction may also be carried out in situ, during the formation of the compositions of formula II.

Hypophosphite Salt

Hypophosphite salts are useful for the preparation of the composition of the present invention may be represented by the formula 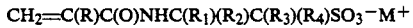 $M^+(^-OP(O)H_2)$ wherein M is $NR_4^+$ or an equivalent metal cation.

Sodium hypophosphite, which is employed in the present method as its stable monohydrate, is the preferred hypophosphite salt for use in the present invention. When sodium hypophosphite is used as the hypophosphite salt, a sodium phosphinate will be isolated as the reaction product. Although it will generally be preferred that the present method be directed toward the preparation of sodium phosphinates due to their high water solubility, stability and low cost, for some applications the preparation of other alkali metal or alkaline earth metal phosphinates may be desirable. In such cases, other alkali metal hypophosphites such as lithium hypophosphite, potassium, hypophosphites, rubidium hypophosphite, or cesium hypophosphite may be employed in the present reaction with the appropriate adjustment in the solvent system, reaction temperature and the like.

In the present method, the final molar ratio of sulfonic acid compound to hypophosphite salt can fall within the range of about 5:1. Most preferably, the molar ratio of sulfonic acid compound to hypophosphite salt will be about 2–1:1.

The Free-Radical Initiator

To prepare the phosphinate compounds in the present invention, a solution of the hypophosphite salt is preferably reacted with the sulfonic acid compound in the presence of an amount of a free-radical source effective to catalyze the reaction between the hypophosphite anion and the vinyl bond of the sulfonic acid compound. Any of the common free-radical sources including organic peroxides such as benzoyl peroxide or diazo compounds such as 2,2'-azobisisobutyronitrile (AIBN) may be employed in the practice of the present invention. Organic peroxyesters are the preferred initiators. Useful commercially-available peroxyesters include the alkylesters of peroxycarboxylic acids, the alkylesters of monoperoxydicarboxylic acids, the dialkylesters of diperoxydicarboxylic acids, the alkylesters of monoperoxycarbonic acids, and the alkylene diesters of peroxycarboxylic acids. Among these classes of peroxyesters, the alkylesters of peroxycarboxylic acids and the alkylesters of monoperoxy dicarboxylic acids have been found to be especially preferred in the practice of the present invention. The former class of peroxyesters includes t-butyl peroctoate, t-butyl perbenzoate and t-butyl peroxyneodecanoate, while the latter class includes compounds such as t-butyl peroxymaleic acid. These compounds are commercially available from Pennwalt Chemicals, Buffalo, NY. The amount of any free-radical initiator required to catalyze the olefin-hypophosphite reaction will vary depending upon the molecular weight of the initiator and its thermal stability. In the case of the peroxyesters, mole ratios of olefin to peroxyester of 5 to 1 or more have been found to provide acceptable reaction rates.

The Solvent System

In the practice of the present invention, the solvent system can be chosen with the decomposition temperature of the reaction promoter in mind. A solution of hypophosphite is typically maintained at a constant temperature while the sulfonic acid compound and the free-radical initiator are simultaneously added into the reaction vessel containing the hypophosphite solution. Preferably, the hypophosphite solution will be maintained at a temperature at or slightly above the decomposition point of the free-radical initiator compound. This temperature will be selected on the basis of the known decomposition temperature of the free-radical initiator compound and will preferably be established by means of a refluxing azeotropic organic solvent system. The most commonly employed azeotropic solvent systems for use in the present invention are mixtures of water and alkanols such as ethanol, methanol, isopropanol and mixtures thereof.

Reaction Methodology

To prepare the phosphinated compositions of the present invention, it is preferable to combine the reagents as taught by U.S. Pat. No. 4,590,014, the disclosure of which is incorporated by reference herein. The hypophosphite salt is first dissolved in the organic solvent system and the solution brought to a temperature at or slightly above the decomposition point of the free-radical initiator compound, e.g., to about 50°–100° C. The sulfonic acid compound and the free-radical initiator are then slowly and simultaneously added to the heated, stirred hypophosphite solution. Preferably, an aqueous solution of the sulfonic acid compound is first converted into the corresponding ammonium, amine or metal salt, by addition thereto of a metal or a nitrogen base. The free-radical initiator compound is dissolved in an organic solvent which is the same as or is compatible with that used to dissolve the hypophosphite salt. Most preferably, separate solvent streams of the sulfonic acid salt and the free-radical initiator are introduced into the hypophosphite solution substantially simultaneously. Once the organic compound and the free-radical initiator have been introduced into the heated hypophosphite solution, the temperature of the reaction mixture, the combined solutions, is maintained at or about the pre-selected temperature for a period of time effective to complete the reaction.

For example, when a peroxyester is employed to initiate the reaction of 2-acryamido-2-methylpropane sodium sulfonate with sodium hypophosphite, the typical post-addition reaction time will be within the ragne of about 0.5 to 6 hours, preferably about 1.5 to 5 hours. At the end of this reaction time, the phosphinate salt is isolated simply by evaporating the solvents and drying the resulting solid salt in vacuo. The extent of reaction between the hypophosphite and the sulfonate salt to form the phosphinate is easily determinable by $^{31}$PNMR. The use of the preferred reaction times in the present method typically provides yields of phosphinate salts on the order of 80 to 100%. Oxidation of the phosphinate product to the corresponding phosphonate product can be accomplished by adding aqueous hydrogen peroxide to the reaction mixture following completion of the initial addition reaction and continuing the heating for an additional 1–6 hours.

The metal, ammonium or amine salts of the compounds of formula II or II which are isolated from the reaction mixture can be reconverted to the corresponding free acids ($M^+ = H^+$) by dissolving them in water and neutralizing or acidifying the solution with a mineral acid such as HCl, $H_2SO_4$, $H_3PO_4$ and the like. Substantially pure compounds of formulas I or II can be isolated by conventional separation techniques such as column chromatography, preparative TLC, HPLC and the like.

The present invention will be further illustrated by reference to the following detailed examples.

EXAMPLE I

A solution of 45.3 g 2-acrylamido-2-methylpropane sulfonic acid (AMPS ™ Monomer, reaction grade, 0.22 moles) in 60 g distilled water, pH adjusted to 12 with 18 g 50% aqueous sodium hydroxide, and a solution of 7.1 g t-butyl peroxyneodecanoate (75%) in 60 g reagent alcohol (95% denatured ethanol plus 5% isopropanol) were simultaneously added drop-wise over a period of two hours to a stirred solution of 13.25 g sodium hypophosphite monohydrate (0.125 moles), 50 g distilled water and 0.10 g of 50% aqueous sodium hydroxide (50%). The temperature was maintained at 85° C. Two hours post-addition, the reaction mixture was evaporated to yield a mixture of products. $^{31}$PNMR indicated a 49:51 mole ratio of $HP(O)(ONa)—CH_2CH_2-C(O)NHC(CH_3)_2CH_2SO_3Na$ to oligomeric materials. Percent conversion based on $^{31}$PNMR was determined to be 80%.

EXAMPLE 2

A solution of 51.75 g 2-acrylamido-2-methylpropane sulfonic acid (AMPS ™ Monomer, reaction grade, 0.25 moles) in 60 g distilled water, pH adjusted to 12 with 21.0 g sodium hydroxide (50%) and a solution of 8.0 g t-butyl peroxyneodecanoate (75%) in 60 g reagent alcohol were simultaneously added drop-wise over a period of two hours to a stirred solution containing 13.25 g sodium hypophosphite monohydrate (0.125 moles), 50.0 g distilled water and 0.10 g sodium hydroxide (50%). The temperature of the reaction mixture was maintained at 85° C. Two hours post-addition, the resulting clear reaction mixture was evaporated to yield a mixture of products. $^{31}$PNMR indicated a 47:53 mole ratio of $HP(O)(ONa)$—$CH_2CH_2C(O)NHC(CH_3)_2CH_2SO_3Na$ to oligomeric materials. Percent conversion was determined to be 90% by $^{31}$PNMR.

EXAMPLE 3

A solution of 77.6 g AMPS TM Monomer (0.375 moles, reaction grade) in 60 g distilled water, pH adjusted to 12 with 32 g sodium hydroxide (50%) and a solution of 12.2 g t-butyl peroxyneodecanoate (75%) in 60 g reagent alcohol were simultaneously added drop-wise over two hours to a stirred solution containing 13.25 g sodium hypophosphite monohydrate (0.125 moles), 50 g distilled water and 0.10 g sodium hydroxide (50%). The temperature of the reaction mixture was maintained at 85° C. Two hours post-addition, the resulting clear reaction mixture was evaporated to yield a mixture of crystalline products. $^{31}$PNMR indicated a 28:72 mole ratio of $HP(O)(ONa)CH_2CH_2C(O)NHC(CH_3)_2CH_2SO_3Na$ to oligomeric materials. Percent conversion based on $^{31}$PNMR was determined to be 91%.

EXAMPLE 4

A solution of 103.5 g AMPS TM Monomer (0.50 moles, reaction grade) in 100 g distilled water, pH adjusted to 12 with 40.5 g sodium hydroxide (50%), and a solution of 16.0 g t-butyl peroxyneodecanoate (75%) in 60 g reagent alcohol were added simultaneously drop-wise over two hours to a stirred solution containing 13.25 g sodium hypophosphite monohydrate (0.125 moles), 50 g distilled water and 0.10 g sodium hydroxide (50%). The reaction temperature was maintained at 85° C. Two hours post-addition, the resulting clear reaction mixture was evaporated to yield a mixture of products. $^{31}$PNMR indicated a 26:74 mole ratio of $HP(O)$—$(ONa)$—$CH_2CH_2CONHC(CH_3)_2CH_2SO_3Na$ to oligomeric materials. Percent conversion based on $^{31}$PNMR was determined to be 90%.

EXAMPLE 5

A solution of 129.38 g AMPS TM Monomer (0.625 moles, reaction grade) in 100 g distilled water, pH adjusted to 12 with 51.5 g sodium hydroxide (50%) and 20 g t-butyl peroxyneodecanoate (75%) in 60 g reagent alcohol were added simultaneously drop-wise over two hours to a stirred solution containing 13.25 g sodium hypophosphite monohydrate (0.125 moles), 50 g distilled water and 0.10 g sodium hydroxide (50%). The reaction temperature was maintained at 85° C. Two hours post-addition, the resulting clear reaction mixture was evaporated to yield a mixture of products. $^{31}$PNMR indicated a 19:81 mole ratio of $HP(O)(ONa)$—$CH_2CH_2CONHC(CH_3)_2CH_2SO_3Na$ to oligomeric materials. Percent conversion based on $^{31}$PNMR was determined to be 90%.

EXAMPLE 6

A solution of 51.75 g AMPS TM Monomer (0.25 moles, reaction grade) in 60 g distilled water, pH adjusted to 7.2 with 20.0 g sodium hydroxide (50%) and a solution of 1.0 g t-butyl peroxyneodecanoate in 15 g reagent alcohol were added drop-wise over a period of two hours to a stirred solution containing 13.25 g sodium hypophosphite monohydrate (0.125 moles) and 50.0 g distilled water. The temperature was maintained at 85° C. One hour post-addition, 24.3 g of hydrogen peroxide (35%) was added. The resulting solution was heated at 85° C. for two additional hours before the solvents were evaporated. $^{31}$PNMR indicated a 43:57 mole ratio of $P(O)(ONa)_2$—$CH_2CH_2CONHC(CH_3)_2CH_2SO_3Na$ to oligomeric materials in the isolated product. Percent conversion based on $^{31}$PNMR was determined to be 70%.

EXAMPLE 7

The ability of five of the products prepared by the procedures of Examples 1–5 supra, to chelate with calcium ion and to prevent its precipitation from aqueous solution as calcium carbonate was determined.

The calcium chelation values of the phosphinates prepared according to the present invention were determined visually by the following procedure. A microscopic stage illuminator lamp was set so that the beam would pass through a 1500 ml beaker at right angles to the analyst's line of sight. One liter of distilled water was introduced into the beaker and 0.2 g of the phosphinate or phosphonate was dissolved in the water. The pH of the solution was measured and adjusted to pH 7 if necessary with 1N sodium hydroxide. Sodium carbonate (1 gram) was added to the solution and the solution pH was adjusted to pH 11 with sodium hydroxide. The phosphonate or phosphinate solution was then titrated with 0.25N calcium acetate solution by adding the calcium acetate solution drop-wise and allowing each drop to fully react before adding the next drop. The end point was reached and the titration discontinued when the Tyndall effect was observed by the analyst at along at least two-thirds of the light beam. The chelation value was calculated by the following formula:

$$\text{Chelation Value(mg CaCO}_3\text{/gm)} = \frac{(\text{ml }^-\text{OAc})(0.25)}{(\text{dry wt. sample})(0.01)}$$

In the above formula (dry weight sample) refers to the dry weight of the phosphinate or phosphonate which was titrated. The results of the titration of 0.2 g sample weights of sodium octyl phosphonate, sodium octyl phosphinate and the compositions of Examples 1–5 are summarized in Table II below:

TABLE II

| Chelator of Example | Chelation Value (mg CaCO$_3$/g of Chelator) |
| --- | --- |
| 1 | 650 |
| 2 | 799 |
| 3 | 779 |
| 4 | 772 |
| 5 | 775 |
| Sodium octyl phosphonate | 650 |
| Sodium octyl phosphinate | 886 |

From the chelation values listed on Table II, it can be seen that for an equivalent weight of chelator in aqueous solution, the compositions of Examples 1–6 were at least as effective in inhibiting the precipitation of calcium carbonate from solution than was sodium octyl phosphonate.

The results summarized on Table II indicate that the water-soluble phosphinate and phosphonate salts of the present invention will be highly effective to complex hardness factors such as calcium and magnesium cations. Thus, it is expected that these compositions will be useful as builders in commercial and consumer detergent products. When used in such formulations, the present phosphinate and phosphonate salts will act to inhibit or prevent the precipitation of inorganic and organic detergent components including builders such as sodium carbonate, sodium tripolyphosphate, sodium bicarbonate, sodium silicate, and the synthetic or natural alkali metal soap or nonsoap detergents. Of course, acids or metal salts of the compounds of formula II or III which are not water-soluble can be readily converted into water-soluble salts such as ammonium or alkali metal salts by the methods described hereinabove.

Although the present invention has been described by reference to certain preferred embodiments, those with skill in the art will recognize that many modifications may be made therein without departing from the spirit and scope of this invention.

What is claimed is:

1. A compound of the formula:

H—P(O)(O$^-$M$^+$)—CH$_2$CH(R)C(O)NH—Z—SO$_3$$^-$M$^+$ or (M$^+$$^-$O)$_2$P(O)—CH$_2$CH(R)C(O)NH—Z—SO$_3$$^-$M$^+$, wherein R is H or (C$_1$-C$_7$)alkyl, M$^+$ is H$^+$, NR$_4$$^+$ or one equivalent of a metal cation, and Z is a divalent (C$_1$-C$_{18}$)hydrocarbyl group.

2. The compound of claim 1 wherein M$^+$ is H$^+$, NH$_4$$^+$, an alkali metal or an alkaline earth metal cation.

3. The compound of claim 2 wherein M$^+$ is H$^+$ or Na$^+$.

4. The compound of claim 1 wherein Z is (C$_1$-C$_{18}$)alkylene, (C$_5$-C$_{10}$)cycloalkylene or (C$_6$-C$_{18}$)arylene.

5. The compound of claim 4 wherein Z is (a) an n-alkylene moiety, (b) an alkyl-substituted-n-alkylene moiety, or (c) a phenyl-substituted alkylene moiety of type (a) or (b) wherein the plenyl moiety is optionally substituted by about 1-3 (C$_1$-C$_4$)alkyl groups.

6. The compound of claim 4 wherein Z is (R$_1$)(R$_2$)C—C(R$_3$)(R$_4$) wherein R$_1$, R$_2$, R$_3$ and R$_4$ are individually (C$_1$-C$_4$)alkyl or (C$_5$-C$_{10}$)cycloalkyl.

7. The compound of claim 4 wherein the (C$_6$-C$_{18}$)arylene moiety is a phenylene or a naphthylene moiety.

8. The compound of claim 4 wherein the arylene moiety is a phenylene attached to 1-2 (C$_1$-C$_4$)alkylene moieties.

9. A compound of the formula:

H—P(O)(O$^-$M$^+$)—CH$_2$CH(R)-C(O)NHC(R$_1$)(R$_2$)C(R$_3$)(R$_4$)SO$_3$$^-$M$^+$ or (M$^+$$^-$O)$_2$P(O)—CH$_2$CH(R)-C(O)NHC(R$_1$)(R$_2$)C(R$_3$)(R$_4$)SO$_3$$^-$M$^+$ wherein R, R$_1$, R$_2$, R$_3$ and R$_4$ are individually H or (C$_1$-C$_4$)alkyl and M$^+$ is H$^+$ or an alkali metal cation.

10. The compound of claim 9 wherein R is H or CH$_3$.

11. The compound of claim 9 wherein M$^+$ is Na$^+$.

12. The compound of claim 9 wherein R$_1$, R$_2$, R$_3$ and R$_4$ are individually H or CH$_3$.

13. The compound of claim 9 wherein R, R$_3$ and R$_4$ are H and R$_1$ and R$_2$ are CH$_3$.

14. A phosphinated sulfonic acid compound which is prepared by a process comprising reacting (a) a hypophosphite salt of the formula: M$^+$($^-$OP(O)H$_2$), wherein M$^+$ is NR$_4$$^+$ or one equivalent of a metal cation, and wherein R is H or (C$_1$-C$_7$)alkyl, with (b) an alkenyl sulfonic acid compound of the formula:

CH$_2$=C(R)C(O)NH—Z—SO$_3$—M$^+$ wherein Z is a divalent (C$_1$-C$_{18}$)hydrocarbyl group.

15. A phosphonated sulfonic acid compound which is prepared by a process comprising:

(1) reacting (a) a hypophosphite salt of the formula: M$^+$($^-$OP(O)H$_2$), wherein M$^+$ is NR$_4$$^+$ or one equivalent of a metal cation, and wherein R is H or (C$_1$-C$_7$)alkyl, with (b) an alkenyl sulfonic acid compound of the formula:

CH$_2$=C(R)C(O)NH—Z—SO$_3$—M$^+$ wherein Z is a divalent (C$_1$-C$_{18}$)hydrocarbyl group to yield a phosphinated sulfonic acid compound; and (2) oxidizing the phosphinated sulfonic acid compound to the corresponding phosphonated sulfonic acid compound.

* * * * *